United States Patent [19]

Verdicchio et al.

[11] 3,950,417

[45] Apr. 13, 1976

[54] HIGH-LATHERING NON-IRRITATING DETERGENT COMPOSITIONS

[75] Inventors: Robert J. Verdicchio, Succasunna; John M. Walts, Clark, both of N.J.

[73] Assignee: Johnson & Johnson, New Brunswick, N.J.

[22] Filed: Feb. 28, 1975

[21] Appl. No.: 553,952

[52] U.S. Cl. ........... 252/545; 252/547; 252/DIG. 7; 424/70
[51] Int. Cl.² .................... C11D 1/831; C11D 1/84
[58] Field of Search 252/545, 547, DIG. 7, DIG. 13; 260/501.11, 501.13; 424/70

[56] References Cited
UNITED STATES PATENTS

| | | | |
|---|---|---|---|
| 3,055,836 | 9/1962 | Masci et al. | 252/545 |
| 3,280,179 | 10/1966 | Ernst | 252/DIG. 7 |
| 3,755,559 | 8/1973 | Hewitt | 252/545 |

*Primary Examiner*—William E. Schulz

[57] ABSTRACT

High lathering detergent compositions having excellent foam stability and low ocular irritation comprise a member selected from the group consisting of surfactant alkylbetaines, alkylamidobetaines, alkylsulfobetaines, and alkylamidosulfobetaines; and anionic surfactant; and a water-soluble, polyoxyethylene derivative of a hydrophobic base as the nonionic surfactant in a weight ratio of about 1:1:3, respectively.

12 Claims, No Drawings

HIGH-LATHERING NON-IRRITATING DETERGENT COMPOSITIONS

BACKGROUND OF THE INVENTION

The present invention relates to detergent compositions and shampoos, and more particularly to those detergent compositions and shampoos which have relatively low ocular irritation and yet have large foam volume and improved foam stability.

Detergent compositions, like most types of liquid cleaning agents, generally comprise a mixture of one or more surfactants as the active ingredient, perfumes, coloring agents, thickeners, etc. The surfactants have two portions: 1) hydrophobic hydrocarbon chain miscible with organic materials and 2) a hydrophilic end-group miscible with water. When such a surfactant contacts a particle of soil, the hydrocarbon chains mix therewith and the hydrophilic end-groups are presented to the aqueous solution. This process of emulsification allows the soil, which otherwise would resist removal by the water, to be cleaned from the body thereby. The surfactants may be classified as anionic, cationic, nonionic, or amphoteric, depending upon the character of the end-groups.

It is desirable that detergent compositions have high foam volume and foam stability, particularly if they are used as shampoos. The amount of foam or lather produced by a shampoo has a direct bearing on the perceived efficiency with which it cleans the hair. The stability of that foam indicates how long it will keep the hair lathered. Generally speaking, the larger the volume of foam produced and the more stable the foam, the more efficient the perceived cleaning action of the shampoo.

A further desirable property for a shampoo, especially one designed for use by children, is that it have low ocular irritation. Because a shampoo may accidentally contact the ocular mucosa during use, especially use by children, one which causes relatively little irritation is both desirable and useful. Such non-irritating shampoos are known, see for example Masci, et al., U.S. Pat. No. 3,055,836, but these generally have poor foam stability.

Surfactant betaines are generally known as amphoteric surfactants useful in detergent compositions. See, for example, U.S. Pat. No. 3,280,179, which teaches that high-lathering detergent compositions may be prepared by replacing some or all of the anionic or cationic surfactant in conventional shampoo formulations by the acyclic sulfobetaine disclosed therein or by incorporating the latter into conventional soaps. But while these compositions have large foam volume and foam stability, they are severe ocular irritants and hence are unsuitable for use by children or others who desire a non-irritating shampoo. Although a low-irritation, high foam shampoo comprising a betaine and other amphoteric surfactants has supposedly been suggested by Ceccarelli and Proserpio [Riv. Ital. Essenze, 59(9):573-577 (1971)], applicants' following of this teaching yielded a shampoo which is a severe ocular irritant. While applicants recognizes that the use of surfactant betaines in detergent compositions is taught by these publications, there is no suggestion of the formulations of the present invention, which combine high foam and good foam stability with low ocular irritation.

SUMMARY OF THE INVENTION

Now it has been discovered that a detergent composition comprising a surfactant betaine (as defined below), an anionic surfactant, and a water soluble, polyoxyethylene derivative of a hydrophobic base as the nonionic surfactant is relatively non-irritating to the eye while providing high foam volume and improved foam stability.

As used herein, the term "surfactant betaine" means compounds having the formula:

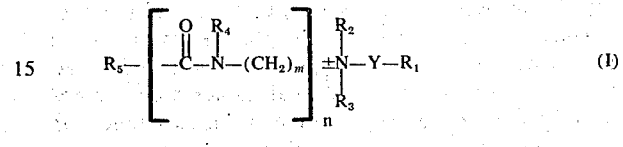

Wherein:
$R_1$ is a member selected from the group consisting of

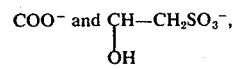

$R_2$ is loweralkyl;
$R_3$ is loweralkyl;
$R_4$ is a member selected from the group consisting of hydrogen and loweralkyl;
$R_5$ is higher alkyl;
Y is loweralkyl, preferably methyl;
$m$ is an integer from 2 to 7; and
$n$ is the integer 1 or 0.

The term "alkali metal" is generic to lithium, sodium, and potassium. The term "alkaline earth metal" is generic to beryllium, magnesium, calcium, strontium, and barium. The term "loweralkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl" means straight or branch chained saturated and unsaturated aliphatic hydrocarbon radicals having from about eight to about 20 carbon atoms such as, for example, lauryl, cetyl, stearyl, oleyl, and the like. It should be understood that the term "higheralkyl" includes mixtures of a high molecular weight alkyl radicals which may contain one or more intermediate linkages such as ether or polyether linkages or non-functional substitutents such as hydroxyl or halogen radicals which do not affect the hydrophobic character of the radical.

Examples of surfactant betaines of formula (I) wherein n is zero which are useful herein include the alkylbetaines such as cocodimethylcarboxymethylbetaine, lauryldimethylcarboxymethylbetaine, lauryldimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylebetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Surfactant amido betaines and amidosulfo betaines useful in the present invention are exemplified by compounds of formula (I) wherein n is one but otherwise corresponding to the above examples. Examples of surfactant betaines of formula (I) wherein n is one which are useful herein include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, etc. The amidosulfobetaines may be represented by cocoamidodimethylsulfopropylbetaine, stearylamidodimethylsulfopropylbetaine, laurylamidobis-(2-hydroxyethyl)-sulfopropylbetaine, and the like.

The preferred betaine in the present invention is a member selected from the group consisting of surfactant amidocarboxybetaines and amidosulfobetaines. More preferred betaines are the surfactant amidocarboxybetaines, particularly stripped cocoamidodimethylcarboxymethylbetaine, sold by Goldschmidt Co. under the trade name Tegobetaine C. This most preferred betaine has the formula:

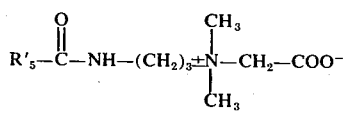

wherein R'$_5$ is a mixture of C8 to C18 alkyl radicals derived from single distilled stripped coconut oil, the majority of said alkyl radicals being C12.

It is envisioned that any anionic surfactant may be used in the detergent composition of the invention such as, for example, an alkyl sulfate of formula R—CH$_2$—OSO$_3$X, an alkylether sulfate of formula R(OCH$_2$CH$_2$)$_p$—OSO$_3$X, an alkylmonoglyceryl ether sulfonate of formula

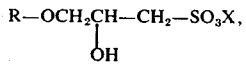

an alkyl monoglyceride sulfate of formula

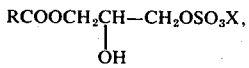

an alkyl monoglyceride sulfonate of formula

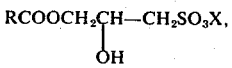

an alkyl sulfonate of formula RSO$_3$X, an alkylaryl sulfonate of formula

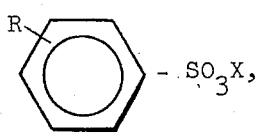

an alkyl sulfosuccinate of formula

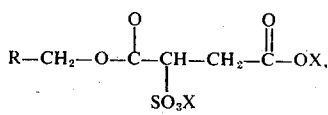

an alkyl sarcosinate of formula

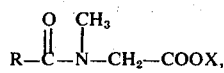

an acyl isethionate of formula

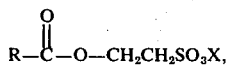

an alkyl methyl tauride of formula

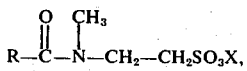

a fatty acid protein condensate of formula

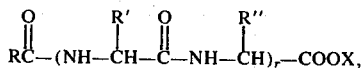

an alcohol ether carboxylate of formula R(CH$_2$CH$_2$O)$_q$—COOX, and the like; wherein R is a higheralkyl having from 8 to 18 carbon atoms; R' and R'' are members each selected from the group consisting of hydrogen, loweralkyl, hydroxyloweralkyl, thioloweralkyl, carboxylower-alkyl, aminoloweralkyl, benzyl, and p-hydroxybenzyl; X is a member selected from the group consisting of alkali metal ions, alkaline earth metal ions, ammonium ions, and ammonium ions substituted with from one to three loweralkyls; $p$ is an integer from about 2 to about 6; $q$ is an integer from 2 to about 6 and $r$ is an integer from 2 to 10.

The preferred type of anionic surfactant is an alkyl ether sulfate, more preferably sodium tridecylalcohol ether sulfate in which q is about 4.4, known as tridecyl alcohol ether (4.4) sulfate.

The nonionic surfactant of the invention is a water-soluble polyoxyethylene derivative of a hydrophobic base, said derivative being a member of the group consisting of:

a. The reaction products of 9-20 carbon atom fatty acid monoesters of aliphatic polyhydric alcohols, which polyhydric alcohols contain at least 3 hydroxyls, with at least 10 moles of ethylene oxide, b. The reaction products of 9-20 carbon atom alcohols, acids and mercaptans with at least two-thirds as many ethylene oxide units as the number of carbon atoms in the hydrophobic base, c. The reaction products of 12-24 carbon atom alkylphenols and alkylcylohexanols with at least as many ethylene oxide units as the number of carbon atoms in the hydrophobic base, and d. Block copolymers of propylene oxide and ethylene oxide having the formula:

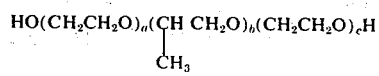

Wherein $a$ is an integer greater than seven, $b$ is an integer from about five to about 20, and $c$ is an integer, all such that ($a$ plus $c$) is at least equal to $b$ and is preferably at least twice $b$. This latter condition on the structure of useful block copolymers is designed to include only those which are sufficiently hydrophilic to give adequate stable foam. The useful block copolymers should also have a molecular weight from about 1,000 to about 20,000.

The preferred type of nonionic surfactant is a member selected from class "$a$", above, more preferably polyoxyethylene sorbitan monolaurate having about 44 polyoxyethylene moieties, called polyoxyethylene (44) sorbitan monolaurate. This preferred nonionic surfactant is a complex mixture, the hydrophobe of which is derived from single distilled stripped coconut oil.

The detergent composition of the invention comprises a surfactant betaine, an anionic surfactant, and a nonionic surfactant in a certain relationship to be defined below. Applicants believe, without intending to be bound thereby, that the amphoteric surfactant betaine and the anionic surfactant form a 1:1 complex in the detergent composition of the invention. It is therefore preferred that the molar ratio of surfactant betaine to anionic surfactant fall between about 0.9 and about 1.1. A slight molar excess of betaine is more preferred. If the betaine and the anionic surfactant are selected to have similar molecular weights then formulation of the detergent composition in terms of equal weights, thereof is valid. Should there be a significant disparity between their molecular weights, however, an equimolar formulation must be used. While a molar ratio between the above values is preferred, one could deviate therefrom at the cost of a slight increase in ocular irritation.

Considered in terms of this complex or combination of surfactant betaine and anionic surfactant, the nonionic surfactant comprises from about 0.5 to about 2.5 times the combined weight of said surfactant betaine and said anionic surfactant, preferably from about one to about two times, and most preferably about 1.5 times. If the surfactant betaine and the anionic surfactant are selected to have substantially similar molecular weights, as the preferred surfactant betaines and anionic surfactants do, than the ratio of surfactant betaine to anionic surfactant to nonionic surfactant should be from about 1:1:1 to 1:1:5, preferably from about 1:1:2 to 1:1:4, and more preferably about 1:1:3.

The detergent compositions of the invention are prepared by first mixing the surfactant betaine and the anionic surfactant at ambient temperature until a homogeneous mixture is formed, and then adding the nonionic surfactant and mixing the whole at elevated temperatures (about 50°C) for about ten minutes until a homogeneous mixture is formed. The pH is then adjusted to 7.2 ± 0.3 by addition of a strong acid (e.g. hydrochloric acid) or a strong base (e.g. aqueous sodium hydroxide solution) as needed.

It is of course contemplated, and considered to be a part of the present invention, that one could use more than one of the surfactant betaines, or more than one of the anionic surfactants, or more than one of the nonionic surfactants in the detergent composition of the invention so long as the above teaching about relative amounts of each type of surfactant is followed.

The detergent compositions of the invention may be used to clean hair and produce high foam volume and good foam stability while also having low ocular irritation. The detergent compositions of the invention may also be used as liquid soaps or cleansers for cleaning other parts of the human body, animals, inanimate objects and the like.

The detergent compositions of the invention may be combined with water or other suitable solvents to yield the high lathering shampoos of the invention, which have good foam stability and low ocular irritation.

The shampoo of the invention comprises from about 2 to about 15 percent by weight of surfactant betaine, from about 2 to about 15 percent by weight of anionic surfactant, and from about 5 to about 30 percent by weight of nonionic surfactant based upon the weight of the entire composition. The remainder of the shampoo is essentially water, but the shampoo may also contain thickeners, dyes, perfumes, preservatives, pH adjusters, and the like, as desired. The preferred compositions for the shampoo of the invention is from about 2 to about 8 percent by weight of surfactant betaine, from about 2 to about 8 percent by weight of anionic surfactant and from about 10 to about 20 percent by weight of nonionic surfactant based on the weight of the composition. The most preferred shampoo comprises about 5 percent by weight of surfactant betaine, about 5 percent by weight of anionic surfactant betaine, and about 15 percent by weight of nonionic surfactant based on the weight of the composition.

The shampoo of the invention is prepared by mixing the surfactant betaine and the anionic surfactant together with a small amount of deionized water, preferably at ambient temperature, to form the above-mentioned complex. Then the nonionic surfactant and a thickener (if desired) are mixed in. Elevated temperatures may be employes at this stage to promote easier mixing of the ingredients. Then more deionized water is mixed in to bring the weight of the composition to about three-quarters of its final weight, and the pH is adjusted to 7.2±0.3 by addition of a mineral acid (e.g., hydrochloric acid) or a solution of a strong base (e.g., sodium hydroxide). Finally, the remainder of the deionized water is added and the pH is again adjusted. Other ingredients, such as preservatives, dyes, perfumes, and the like may be added in any of the last three steps.

The shampoos of the invention possess low ocular irritation as shown by the following modified Draize test (See J. H. Draize, et al., Toilet Goods Associations No. 17, May, 1952, No. 1 Proc. Sci. Sect.):

A 0.1 ml. samples of the neutral composition under test is dropped into one eye of each of six rabbits. Daily administration of the same quantity of each of the samples is continued for 3 consecutive days. Observations are recorded after one hour, one day, two days, three days, four days and seven days after samples are dropped into the eyes. The extremes of the results either show substantially no change or show only a slight irritation (foreign body effect) in the appearance of the rabbits' eyes after seven days, or severe irritation or complete corneal opacity, as the case may be.

The shampoos prepared in Examples I through XII were tested by this procedure and were found to be only slight irritants, even though they each contain about 25 percent by weight of surfactants and would therefore be expected to be severe irritants.

The shampoo of the invention moreover possesses both a high foam volume and foam stability as measured by the following modification of the well-known RossMiles foam test ["Oil and Soap", 18, 99–102

(1941)]:

1. Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45°C. in order to dissolve the lanolin in the dioxane. The remainder of the dioxane is then added and mixed. This lanolin-dioxane solution, which is stored in an amber bottle, should be prepared fresh on the day that the tests are run.

2. The shampoo to be tested is diluted by adding 376 cc. of distilled water to 4 grams of the shampoo, and then adding 20 cc. of the lanolin-dioxane solution described in (1) above while mixing. Heat is produced when the lanolin-dioxane solution is added to the solution of the shampoo in water and care must be taken in adjusting the temperature of this solution to 24°–25°C. Both of these intermediate solutions should therefore be adjusted to 23°C. before mixing. The cooling of the lanolin-dioxane solution should be gradual in order to avoid precipitation of the lanolin. This will produce a final solution with a temperature of 24°–25°C.

3. The final solution of shampoo, water, dioxane and lanolin described in (2) is then run in the Ross-Miles foam column in the usual way. All tests are conducted in duplicate, and the average of the two results is taken.

4. Foam stability is determined by measuring the decay in foam height after five minutes, expressed as a percentage of the original height.

The shampoo of the invention is a superior high-lathering shampoo by this test when compared to, for example, the prior art shampoo of Masci, et al because it exhibits a much smaller percentage decay then the prior art shampoo.

The shampoo of the invention is further described and illustrated in the following examples, which are set forth by way of illustration only and not to limit the scope of the present invention. The betaines in the following examples are 30–32 percent active aqueous solutions. All parts are by weight unless otherwise indicated.

EXAMPLE I

| Ingredients | | % |
|---|---|---|
| (A) | Tegobetaine C[1] | 17.1 |
| | Tridecylalcohol ether sulfate[2] (65% active aqueous solution) | 8.3 |
| | Deionized water | 5.0 |
| (B) | Polyoxyethylene (44) sorbitan monolaurate | 15.0 |
| | Deionized water | 30.0 |
| (C) | Dye | 0.002 |
| (D) | Deionized water, preservation, perfume, and thickener | q.s. |
| | | 100% |

[1]Formula:

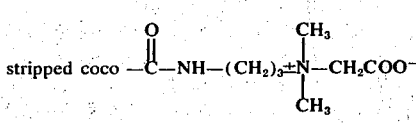

[2]Formula:

  Wherein R is a branched chain aliphatic hydrocarbon having 13 carbon atoms The first three ingredients (Group A) are homogenously mixed at ambient temperature, after which the next ingredient (Group B) is added, and the whole is mixed with heating at 50°C for about 10 minutes until homogeneous. Then the next two ingredients (Group C) are added, the whole is mixed at ambient temperature, and the pH is adjusted to 7.2 ± 0.3 by addition of hydrochloric acid. Finally, the remaining ingredients (Group D) are added and the pH is again adjusted to 7.2 ± 0.3 if necessary, yielding a high lathering shampoo with excellent foam stability and low ocular irritation.

EXAMPLE II

| Ingredients: | | % |
|---|---|---|
| (A) | Lonzaine CS[1] | 19.0 |
| | Tridecylalcohol ether sulfate (as in Example I) | 9.2 |
| | Deionized water | 5.1 |
| (B) | Polyoxyethylene (40) sorbitan monolaurate | 12.6 |
| (C) | Deionized water | 30.0 |
| (D) | Dye, perfume, deionized water, preservatives, and thickener | q.s. |
| | | 100% |

[1]Formula:

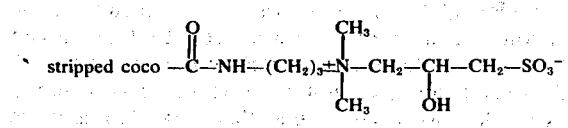

The ingredients are combined as in Example I to yield a high-lathering shampoo with very good foam stability and low ocular irritation.

EXAMPLE III

| Ingredients: | | % |
|---|---|---|
| (A) | Lonzaine CS (as in Example II) | 17.0 |
| | Tridecylalcohol ether sulfate (as in Example I) | 8.2 |
| | Deionized water | |
| (B) | Polyoxyethylene (20) sorbitan monolaurate | 12.6 |
| | Deionized water | 30.0 |
| (C) | Dye | 0.5 |
| (D) | Deionized water, perfume, preservatives, and thickener | q.s. |
| | | 100% |

The ingredients are combined as in Example I to yield a high-lathering shampoo with acceptable foam stability and low ocular irritation.

EXAMPLE IV

Example III is repeated substituting tridecyl alcohol ether sulfate of formula R—O[CH$_2$ CH$_2$O]$_3$SO$_3^-$ for that used therein, wherein R is as defined in Example I. The resulting shampoo is high-lathering and has acceptable foam stability and low ocular irritation.

EXAMPLE V

Following the procedure of Example III, but substituting Lonzaine C (formula: stripped coco —C(=O)—NH—(CH$_2$)$_3$—$\overset{+}{N}$(CH$_3$)$_2$—COO$^-$)

for the Lonzaine CS used therein, a high-lathering shampoo is produced which has very good foam stability and low ocular irritation.

EXAMPLE VI

Following the procedure of Example V, but substituting the tridecylalcohol ether sulfate of Example IV for that used therein, a high-lathering shampoo is produced which has very good foam stability and low ocular irritation.

EXAMPLE VII

| Ingredients: | | % |
|---|---|---|
| (A) | Varion CADG[1] | 17.2 |
| | Tridecylalcohol ether sulfate (As in Example I) | 15.7 |
| | Deionized water | 4.5 |
| (B) | Polyoxyethylene (83) sorbitan monolaurate | 15.0 |
| (C) | Deionized water | 30.0 |
| | Dye | 0.5 |
| (D) | Deionized water, perfume, preservatives, and thickeners | q.s. |
| | | 100% |

[1]Formula:

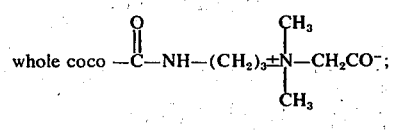

whole coco $-\overset{O}{\underset{\|}{C}}-NH-(CH_2)_3\overset{CH_3}{\underset{CH_3}{\overset{|}{\pm}N}}-CH_2CO^-$;

Ashland Chemical Company

The ingredients are combined as in Example I, but using sodium hydroxide solution to adjust the pH, to yield a high-lathering shampoo with excellent foam stability and low ocular irritation.

EXAMPLE VIII

The procedure of Example VII is repeated twice, except that the first time only 12.0% polyoxyethylene (44) sorbitan monolaurate is used instead of 15.0% and the second time 12.0% of a propylene oxideethylene oxide block copolymer sold by Wyandotte Co. under the name Pluronic F-68 is substituted for the 15.0% polyoxyethylene (44) sorbitan monolaurate used therein. In both repetitions, high-lathering shampoos having excellent foam stability and low ocular irritation are produced.

EXAMPLE IX

| Ingredients: | | % |
|---|---|---|
| (A) | Tegobetaine C | 17.0 |
| | Tridecylalcohol ether sulfate (as in Example I) | 8.3 |
| | Deionized water | 5.0 |
| (B) | Polyoxyethylene (44) sorbitan monolaurate | 15.0 |
| (C) | Deionized water | 30.0 |
| | Dye | 0.5 |
| (D) | Deionized water, perfume, preservatives, and thickeners | q.s. |
| | | 100% |

The ingredients are combined as in Example I, except that sodium hydroxide solution is used instead of hydrochloric acid to correct pH, to yield a high lathering shampoo with very good foam stability and low ocular irritation.

EXAMPLE X

The procedure of Example IX is repeated, except that Tegobetaine L

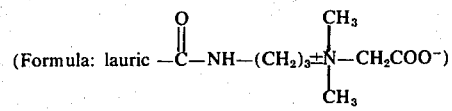

(Formula: lauric $-\overset{O}{\underset{\|}{C}}-NH-(CH_2)_3\overset{CH_3}{\underset{CH_3}{\overset{|}{\pm}N}}-CH_2COO^-$)

is substituted for the Tegobetaine C used therein, to yield a high-lathering shampoo with excellent foam stability and low ocular irritation.

EXAMPLE XI

| Ingredients: | | % |
|---|---|---|
| (A) | Lonzaine 12CS[1] | 17.1 |
| | Tridecylalcohol ether sulfate (As in Example I) | 8.3 |
| | Deionized water | 5.0 |
| (B) | Polyoxyethylene (20) sorbitan monolaurate | 12.7 |
| (C) | Deionized water | 30.0 |
| | Dye | 0.5 |
| (D) | Deionized water, perfume, preservatives, and thickeners | q.s. |
| | | 100% |

[1]Formula:

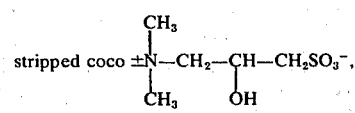

stripped coco $\pm\overset{CH_3}{\underset{CH_3}{\overset{|}{N}}}-CH_2-\underset{OH}{\overset{|}{C}H}-CH_2SO_3^-$, The ingredients are combined as in Examine I, except that sodium hydroxide solution is used instead of hydrochloric acid to correct pH, yielding a high lathering shampoo with excellent foam stability and low ocular irritation.

EXAMPLE XII

| Ingredients: | | % |
|---|---|---|
| (A) | Carboxybetaine[1] | 15.0 |
| | Tridecylalcohol ether sulfate (as in Example I) | 15.0 |
| | Deionized water | 5.0 |
| (B) | Polyoxyethylene (20) sorbitan monolaurate | 12.6 |
| (C) | Deionized water | 30.0 |
| | Dye | 0.5 |
| (D) | Deionized water, preservatives, perfumes, and thickeners | q.s. |
| | | 100% |

[1]Formula:

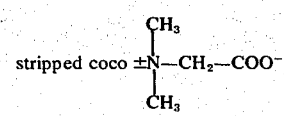

stripped coco $\pm\overset{CH_3}{\underset{CH_3}{\overset{|}{N}}}-CH_2-COO^-$

The ingredients are combined as in Example I to yield a high lathering shampoo with good foam stability and low ocular irritation.

EXAMPLE XIII

The shampoos prepared in Examples I-XII are all tested for foam volume and foam stability by the Ross-Miles foam test described above. The results are tabulated below.

| EXAMPLE | FOAM HEIGHT (MM) | % DECAY (5 MIN.) |
|---|---|---|
| I | 126 | 5% |
| II | 131 | 10% |
| III | 85 | 41% |
| IV | 91 | 40% |
| V | 90 | 15% |
| VI | 88 | 14% |
| VII | 111 | 11% |
| VIIIA | 92 | 7% |
| VIIIB | 113 | 5% |
| IX | 99 | 19% |
| X | 111.5 | 7.5% |
| XI | 95 | 15% |
| XII | 90 | 25% |

For comparison, the prior art non-irritating shampoos of the Masci, et al., Patent exhibit about 50 percent decay in foam height after 5 minutes.

EXAMPLE XIV

Example I is repeated, but using 25.0 parts of polyoxyethylene (44) sorbitan monolaurate in place of the 15.0 parts used therein. The resulting high lathering shampoo has low ocular irritation and good foam stability.

EXAMPLE XV

| Ingredients: | % |
|---|---|
| Lonzaine CS[1] | 42.0 |
| Tridecylalcohol ether sulfate (as in Example I) | 21.0 |
| Polyoxyethylene (40) sorbitan monolaurate | 28.0 |
| Dye, perfume, preservatives, and thickeners | q.s. |
| | 100% |

[1]Formula:

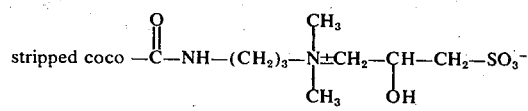

The first two ingredients are combined together and mixed, after which the rest are added and the whole is mixed with heating at 50°C for about ten minutes until homogeneous. The pH is adjusted to 7.2 ±0.3, yielding a high lathering detergent composition with good foam stability and low ocular irritation.

EXAMPLE XVI

| | Ingredients: | % |
|---|---|---|
| (A) | Tegobetaine J (as in Example I) | 40.0 |
| (B) | Tridecylalcohol ether sulfate (as in Example I) | 18.5 |
| | Polyoxyethylene (44) sorbitan monolaurate | 30.0 |
| (C) | Dye | 0.002 |
| (D) | Deionized water, preservatives, perfume and thickeners | q.s. |
| | | 100% |

The ingredients are combined as in Example I to yield a high lathering shampoo with good foam stability and low ocular irritation.

EXAMPLE XVII

The procedure of Example I is repeated, but substituting an equal weight of polyoxyethylene (80) sorbitan monolaurate for the polyoxyethylene (44) sorbitan monolaurate used therein. The resulting high lathering shampoo has low ocular irritation and excellent foam stability.

EXAMPLE XVIII

| | Ingredients: | % |
|---|---|---|
| (A) | Tegobetaine C | 17.0 |
| | Tridecylalcohol (4.4) ether sulfate | 8.3 |
| | Deionized water | 5.0 |
| (B) | Polyoxyethylene (100) sorbitan monolaurate | 7.5 |
| | Polyoxyethylene (80) sorbitan monolaurate | 7.5 |
| (C) | Deionized water | 30.0 |
| | Dye | 0.002 |
| (D) | Deionized water, preservatives, and perfume | q.s. |
| | | 100% |

The ingredients are combined as in Example I to yield a high lathering shampoo with excellent foam stability and low ocular irritation.

EXAMPLE XIX

| | Ingredients: | % |
|---|---|---|
| (A) | Tegobetaine C | 17.1 |
| | Tridecylalcohol (4.4) ether sulfate | 8.3 |
| | Deionized water | 5.0 |
| (B) | Polyoxyethylene (44) sorbitan monolaurate | 9.0 |
| | Polyoxyethylene (80) sorbitan monopalmitate | 6.0 |
| (C) | Deionized water | 30.0 |
| | Dye | 0.002 |
| (D) | Deionized water, preservatives, and perfume | q.s. |
| | | 100% |

The ingredients are combined as in Example I to yield a high lathering shampoo with excellent foam stability and low ocular irritation.

While the above examples have been given for illustrative purposes, one skilled in the art could make many modifications and deviations therefrom within the scope of the present invention, which scope is defined only in the appended claims.

I claim:

1. A detergent composition having good foam stability and low ocular irritation consisting essentially of:

a. a surfactant betaine having the formula:

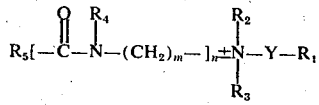

wherein $R_1$ is a member selected from the group consisting of

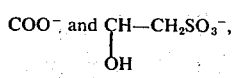

$R_2$ is loweralkyl,
$R_3$ is loweralkyl,

R₄ is a member selected from the group consisting of hydrogen and loweralkyl,
R₅ is higher alkyl,
Y is loweralkyl,
m is an integer from 2 to 7, and
n is the integer 1 or 0;
b. an anionic surfactant; and
c. a polyoxyethylene derivative of a hydrophobic base as nonionic surfactant,
the molar ratio of said surfactant betaine to said anionic surfactant being from about 0.9:1 to about 1.1:1 and the weight of said nonionic surfactant being from about 0.5 to about 2.5 times the combined weight of said surfactant betaine and said anionic surfactant.

2. A detergent composition as in claim 1 wherein the anionic surfactant is an alkyl ether sulfate of formula

wherein R is higher alkyl; p is an integer from about 2 to about 6; and X is a member selected from the group consisting of alkali metal ions, alkaline earth metal ions, ammonium ions, and ammonium ions substituted with from one to three loweralkyls.

3. A detergent composition as in claim 1 wherein the nonionic surfactant is a member selected from the group consisting of the reaction products of 9–20 carbon atom fatty acid monoesters of aliphatic polyhydric alcohols, which polyhydric alcohols contain at least three hydroxyls, with at least ten moles of ethylene oxide.

4. A detergent composition as in claim 1 wherein the surfactant betaine has the formula:

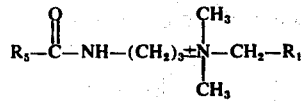

5. A detergent composition having good foam stability and low ocular irritation which consists essentially of:
a. a surfactant betaine having the formula:

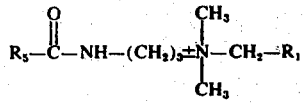

wherein:
R₁ is a member selected from the group consisting of COO- and and 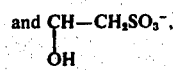

and
R₅ is higher alkyl;
b. an alkyl ether sulfate of formula:

wherein:
R is higher alkyl;
p is an integer from about 2 to about 6; and
X is a member selected from the group consisting of alkali metal ions, alkaline earth metal ions, ammonium ions, and ammonium ions substituted with from one to three loweralkyls;
as anionic surfactant; and
c. a polyoxyethylene derivative of a hydrophobic base as nonionic surfactant, the molar ratio of said surfactant betaine to said anionic surfactant being from about 0.9:1 to about 1.1:1 and the weight of said nonionic surfactant being from about one to about two times the combined weight of said surfactant betaine and said anionic surfactant.

6. A detergent composition as in claim 5 wherein said surfactant betaine has the formula:

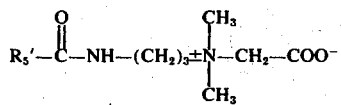

wherein R'₅ is derived from single-distilled stripped coconut oil.

7. A high-lathering shampoo having good foam stability and low ocular irritation which comprises:
a. a surfactant betaine having the formula:

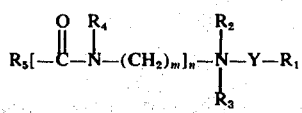

wherein
R₁ is a member selected from the group consisting of COO - and

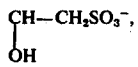

R₂ is loweralkyl,
R₃ is loweralkyl,
R₄ is a member selected from the group consisting of hydrogen and loweralkyl,
R₅ is higher alkyl,
Y is loweralkyl,
m is an integer from 2 to 7, and
n is the integer 1 or 0;
b. an anionic surfactant; and
c. a polyoxyethylene derivative of a hydrophobic base as nonionic surfactant,
the molar ratio of said surfactant betaine to said anionic surfactant being from about 0.9:1 to about 1.1:1, and the weight of said nonionic surfactant being from about 0.5 to about 2.5 times the combined weight of said surfactant betaine and said anionic surfactant, said surfactant betaine comprising from about 2 to about 15 percent by weight of the weight of the shampoo, said anionic surfactant comprising from about 2 to about 15 percent by weight of the weight of the shampoo, and said nonionic surfactant comprising from about 5 to about 30 percent by weight of the weight of the shampoo.

8. A shampoo as in claim 7 wherein the anionic surfactant is an alkyl ether sulfate of formula:

wherein R is higher alkyl; p is an integer from about 2 to about 6; and X is a member selected from the group consisting of alkali metal ions, alkaline earth metal ions, ammonium ions, and ammonium ions substituted with from one to three loweralkyls.

9. A shampoo as in claim 7 wherein the nonionic surfactant is a member selected from the group consisting of the reaction products of 9–20 carbon atom fatty acid monoesters of aliphatic polyhydric alcohols, which polyhydric alcohols contain at least three hydroxyls, with at least ten moles of ethylene oxide.

10. A shampoo as in claim 7 wherein the surfactant betaine has the formula:

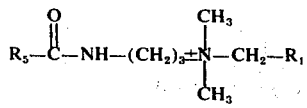

11. A shampoo having good foam stability and low ocular irritation which consist essentially of:
a. a surfactant betaine having the formula:

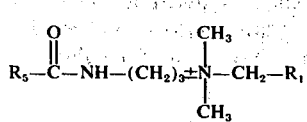

wherein:
R$_1$ is a member selected from the group consisting of COO$^-$

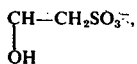

and
R$_5$ is higher alkyl;

b. an alkyl ether sulfate of formula:

$$R(OCH_2CH_2)_pOSO_3X$$

wherein:
R is higher alkyl;
p is an integer from about 2 to about 6; and
X is a member selected from the group consisting of alkali metal ions, alkaline earth metal ions, ammonium ions, and ammonium ions substituted with from one to three loweralkyls;
as anionic surfactant; and
c. a polyoxyethylene derivative of a hydrophobic base as nonionic surfactant,
the molar ratio of said surfactant betaine to said anionic surfactant being from about 0.9:1 to about 1.1:1 and the weight of said nonionic surfactant being from about one to about two times the combined weight of said surfactant betaine and said anionic surfactant, said surfactant betaine comprising from about 2 to about 8 percent by weight of the weight of the shampoo, said anionic surfactant comprising from about 2 to about 8 percent by weight of the weight of the shampoo, and said nonionic surfactant comprising from about 10 to about 20 percent by weight of the weight of the shampoo.

12. A shampoo as in claim 11 wherein said surfactant betaine has the formula:

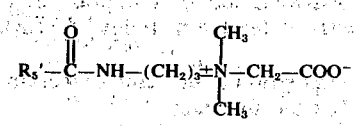

wherein R'$_5$ is derived from single distilled stripped coconut oil.

* * * * *